Figure 1:
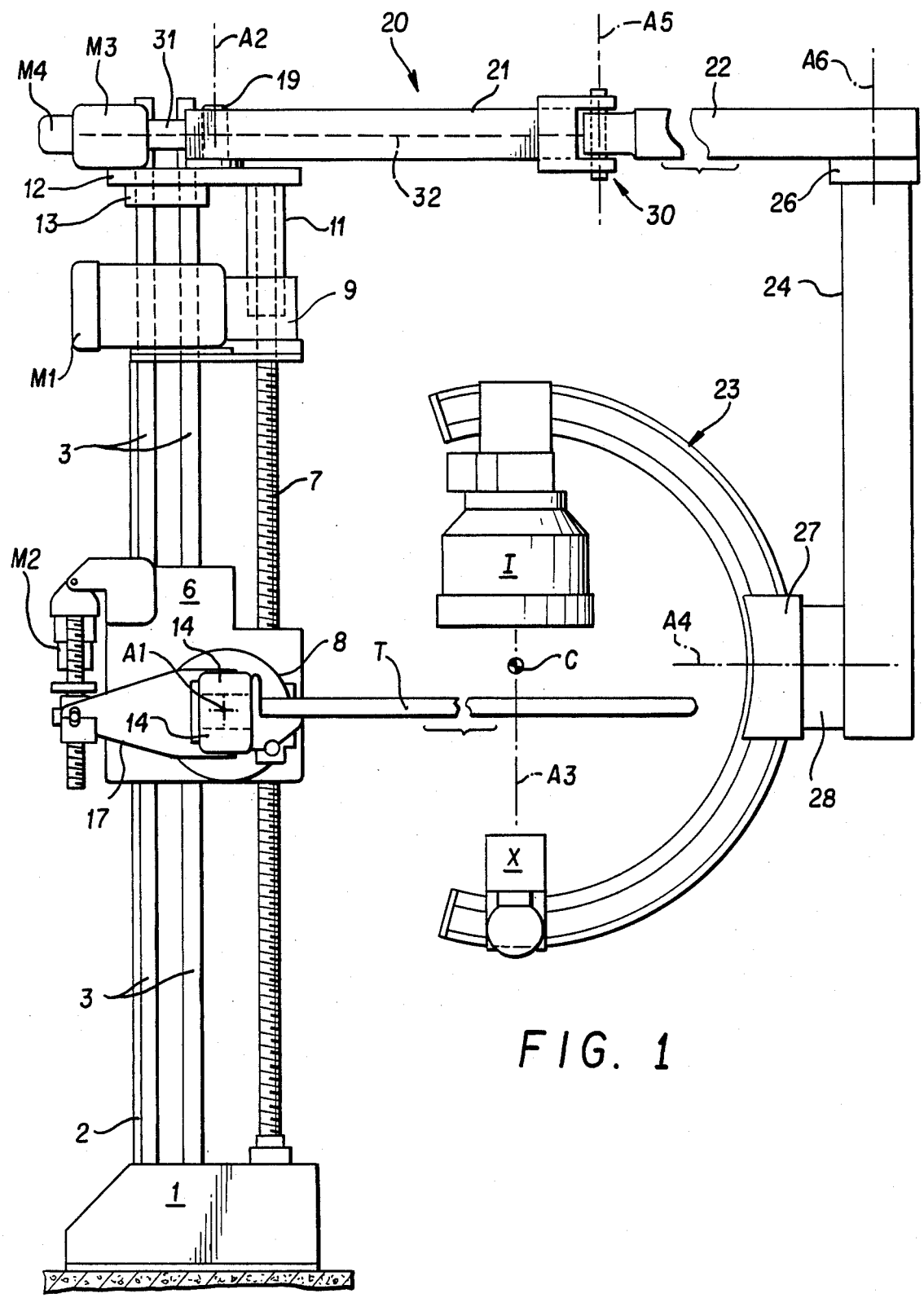

United States Patent [19]

Grady

[11] Patent Number: 4,879,737
[45] Date of Patent: Nov. 7, 1989

[54] ARTICULATED X-RAY STAND ARM

[76] Inventor: John K. Grady, XRE Corporation, 300 Foster St., Littleton, Mass. 01460

[21] Appl. No.: 322,499

[22] Filed: Mar. 13, 1989

[51] Int. Cl.$^4$ .............................................. H05G 1/02
[52] U.S. Cl. ...................................... 378/196; 378/195
[58] Field of Search ................ 378/195, 196, 197, 198

[56] References Cited

U.S. PATENT DOCUMENTS 4,716,581  12/1987  Barud ................................. 378/197
4,775,994  10/1988  Kranvogel ......................... 378/197

Primary Examiner—Craig E. Church

Attorney, Agent, or Firm—James H. Grover

[57] ABSTRACT

X-ray apparatus for examination of a patient comprises an upright standard, a patient table extending laterally from the standard, a two-limbed support carrying an X-radiation source on one limb and an X-radiation receptor on the other limb and a generally horizontal arm pivoted at one end to the standard on a first vertical axis and extending from the pivoted end at the standard to a free end connected to the two-limbed support so as to hold the source and receptor on a radiation axis through the table, the arm being articulately jointed intermediate the standard and support so as to selectively position the support at either side of the table.

7 Claims, 2 Drawing Sheets

ARTICULATED X-RAY STAND ARM

BACKGROUND OF THE INVENTION

In X-ray examination of patients, particularly patients subject to trauma during the examination procedure it is necessary that the doctors and other medical staff attending the examination have unobstructed access to one side of the table supporting the patient. All parts of the X-ray stand carrying the X-ray tube and image intensifier or other X-ray receptor must therefore extend along only one side of the patient table. But the side requiring free access may change during the procedure and prior X-ray stands suitable for trauma procedures have not been practically repositioned from one side of the table to the other. Attempts to provide freer access to the table by suspending the X-ray system from the ceiling involve expensive and extensive structural steelwork which interferes with other operating room systems such as surgical lights.

It is therefore a main object of the present invention to provide an X-ray stand which is quickly and easily repositioned so as to leave either side of the patient table selectively unobstructed. A further object is to avoid the interference and expense of ceiling mounted X-ray systems.

SUMMARY OF THE INVENTION

According to the invention X-ray apparatus for examination of a patient comprises an upright standard, a patient table extending laterally from the standard, a two-limbed support carrying an X-radiation source on one limb and an X-radiation receptor on the other limb, and a generally horizontal arm pivoted at one end to the standard on a first vertical axis and extending from the pivoted end at the standard to a free end connected to the two-limbed support so as to hold the source and receptor on a radiation axis through the table, the arm being articulately jointed intermediate the standard and support so as to selectively position the support at either side of the table. Further the standard includes means for raising and lowering movements of the table and arm, and preferably means for coordinating these movements, while supporting the X-ray system and patient table on a single, floor based standard.

DRAWINGS

Figure 2:
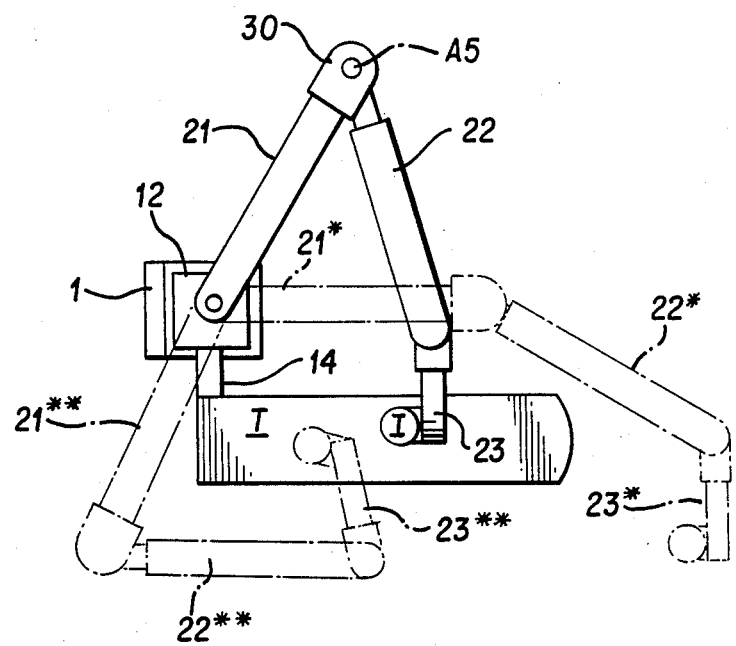

FIG. 1 is a side elevation of an X-ray patient stand according to the invention; and FIG. 2 is a schematic plan view showing alternative positions of the stand.

DESCRIPTION

The X-ray stand in FIG. 1 comprises a base 1 for an upright standard 2. The standard has vertical rails 3 which are engaged by linear bearings 4 on a carriage 6 which is driven up and down on the rails by rotation of a screw 7 engaging the carriage and driven by a first motor M1 through a gearbox 9. The screw extends into a nut 11 secured to a platform 12 with linear bearings 13 engaging the vertical rails 3.

A cantilever beam 14 extending laterally from a rotary bearing 16 on the carriage 6 supports a patient table T at right angles to the beam. The beam is rotated by a bell crank 17 turned by a second motor M2 to tilt the patient table head to foot about a transverse first axis A1. This tilting of the patient table as well as its raising or lowering may require adjustment of the location of an X-ray tube X and image intensifier I as follows.

The X-ray tube X and image intensifier I are carried on a support structure consisting of a generally horizontal arm 20 connected by a pivot pin 19 to the platform 12 so as to rotate about a vertical second axis A2. The arm 20 has two sections 21 and 22 extending from the pivoted end to a free end from which a two-limbed, C-shaped or U-shaped support 23 is suspended by a vertical member 24 attached to the arm section 22 with a rotary bearing 26. One limb of the support carries the image intensifier I, the other carrying the X-ray tube so that the tube and intensifier are aligned on a radiation axis A3 directed through the patient on the table 2. A collar 27 connected to the vertical member 24 by a rotary bearing 28 engages tracks 29 on the C-shaped support allowing the support to rotate the radiation axis A3 about an isocenter C at the intersection of the radiation axis and the axis A4 of rotation of the support through the bearing 28.

According to the present invention the two sections of the horizontal arm connected between the standard 2 and the two-limbed support 23 are articulately jointed by a coupling approximately midway between the pivoted and the free ends of the arm. This articulation allows the free end section 22 of the arm to rotate relative to the other section 21 about an axis intermediate the pivot axis A2 on the standard and the vertical rotational axis A6 through the bearing 26 at the free end of the arm. Rotation about each of the three vertical axes A2, A5, and A6 may be effected by manual positioning of the support, or by drive of the pivoted arm end from a motor M3 through a gear box 31 and drive of the articulate joint by a motor M4 through a linkage 32.

As shown in FIG. 2 the articulate joint of the present X-ray stand permits the two-limbed support 23 for the X-ray tube and receptor to be swung from the solid line position shown at one side of the table T, thence through a first phantom position 21*,22* around the end of the table to a second phantom position 21, 22 at the other side of the table so that either side of the table may be left unobstructed when desired during the continuing X-ray examination procedure, and without interfering with raising or tilting of the patient table if needed to ease patient trauma during the procedure.

It should be understood that the present disclosure is for the purpose of illustration only, and that the invention includes all modifications and equivalents falling within the appended claims.

I claim:

1. X-ray apparatus for examination of a patient comprising:
    an upright standard;
    a patient table extending laterally from the standard;
    a two-limbed support with an X-radiation source on one arm and an X-radiation receptor on the other arm; and
    an arm pivoted to the standard on a first vertical axis and extending the pivot end of the standard to a free end connected to the two-limbed support to hold the source and receptor on a radiation axis through the table, the arm being articulately jointed between its pivoted end and free end on a second vertical axis intermediate the standard and support so as to selectively position the support at either side of the table, while supporting the X-radiation source and receptor and the patient table on a single floor based standard.

2. Apparatus according to claim 1 including an upright member suspending the two-limbed support from the free end of the jointed arm.

3. Apparatus according to claim 2 including a rotary bearing between the upright member and jointed arm for angular adjustment of the two-limbed support and the X-ray source and receptor about a third vertical axis.

4. Apparatus according to claim 1 wherein the table is cantilever mounted on the standard with a free end so as to be approachable from both its longitudinal sides.

5. Apparatus according to claim 4 wherein the arm is of length greater than the table so that the two-limbed support may be swung around the free end of the table.

6. Apparatus according to claim 1 including means on the standard for adjusting the elevation of the jointed arm.

7. Apparatus according to claim 1 including means on the standard for raising and lowering the table, and means coordinating the movements of the table and arm.

* * * * *